(12) United States Patent
Thacker et al.

(10) Patent No.: US 7,321,794 B2
(45) Date of Patent: Jan. 22, 2008

(54) METHOD AND SYSTEM FOR TREATING ATRIAL FIBRILLATION

(75) Inventors: James R Thacker, Eureka, MO (US); Kelly H McClure, Simi Valley, CA (US); Todd K Whitehurst, Santa Clarita, CA (US); Philip H Lee, Santa Clarita, CA (US)

(73) Assignee: Advanced Bionics Corporation, Valencia, CA (US)

( * ) Notice: Subject to any disclaimer, the term of this patent is extended or adjusted under 35 U.S.C. 154(b) by 373 days.

(21) Appl. No.: 10/713,511

(22) Filed: Nov. 14, 2003

(65) Prior Publication Data

US 2004/0230231 A1    Nov. 18, 2004

Related U.S. Application Data

(60) Provisional application No. 60/426,977, filed on Nov. 15, 2002.

(51) Int. Cl.
*A61N 1/368*    (2006.01)

(52) U.S. Cl. ............................................. 607/50; 607/9

(58) Field of Classification Search ................ 607/4–8, 607/14, 15, 50; 600/515–518
See application file for complete search history.

(56) References Cited

U.S. PATENT DOCUMENTS

| | | | |
|---|---|---|---|
| 3,937,226 A | | 2/1976 | Funke |
| 5,334,221 A | | 8/1994 | Bardy |
| 5,356,425 A | | 10/1994 | Bardy et al. |
| 5,403,356 A | * | 4/1995 | Hill et al. ...................... 607/14 |
| 5,620,468 A | * | 4/1997 | Mongeon et al. ............... 607/5 |
| 5,653,734 A | * | 8/1997 | Alt ................................. 607/5 |
| 5,683,429 A | * | 11/1997 | Mehra .......................... 607/14 |
| 6,141,586 A | * | 10/2000 | Mower .......................... 607/9 |
| 6,178,351 B1 | * | 1/2001 | Mower .......................... 607/5 |
| 6,292,694 B1 | * | 9/2001 | Schloss et al. ................. 607/9 |
| 6,952,610 B2 | * | 10/2005 | Ostroff et al. ................ 607/14 |
| 2001/0018600 A1 | * | 8/2001 | Plicchi et al. ................. 607/14 |
| 2004/0088010 A1 | * | 5/2004 | Warman et al. ................ 607/5 |

FOREIGN PATENT DOCUMENTS

WO    WO-92/18198 A2    10/1992

\* cited by examiner

*Primary Examiner*—Mark Bockelman
*Assistant Examiner*—Eric D. Bertram
(74) *Attorney, Agent, or Firm*—Schwegman, Lundberg & Woessner, P.A.

(57) ABSTRACT

An atrial, anti-arrhythmia system and method are provided. The system comprises: at least two electrodes attached to the atrium for providing independently controlled stimulus through each electrode; detection circuitry that can sense atrial fibrillation or the cardiac cycle; and stimulus generator that can deliver stimulation through at least two electrodes to stop atrial fibrillation. The method for treating atrial fibrillation has three possible modes: a first mode for detecting ongoing atrial fibrillation and stopping it; a second mode for detecting the cardiac cycle and delivering stimuli to the atrium after it has already begun to contract in order to suppress the onset of atrial fibrillation; and a third mode which applies pacing pulses to the atrium in a timed sequence to pace and contract the atrium faster than the native rate to preempt the initiation of atrial fibrillation.

20 Claims, 9 Drawing Sheets

METHOD AND SYSTEM FOR TREATING ATRIAL FIBRILLATION

The present application claims the benefit of U.S. Provisional Patent Application Ser.No. 60/426,977, filed 15 Nov. 2002, which application is herein incorporated by reference.

FIELD OF THE INVENTION

The present invention relates to cardiac pacing. More specifically, the present invention relates to methods and systems for treating atrial fibrillation.

BACKGROUND OF THE INVENTION

Atrial fibrillation is associated with formation of emboli which can cause thrombi, strokes, heart attacks, kidney infarcts and pulmonary embolisms. Once atrial fibrillation is initiated, it is often difficult to reverse. An atrium which is in fibrillation does not efficiently pump blood, and as such, the atrium may dilate. Such dilation perpetuates a vicious cycle because the occurrence of atrial fibrillation in a dilated heart is more difficult to reverse than in a normal heart, since a dilated atrium increases the conductive pathway length which further increases the time required to complete one cycle of atrial contraction. A longer, conductive pathway increases the probability of facilitating undesirable conduction circus motions in an atrium.

There have been a number of approaches to treating atrial fibrillation. One approach is a pharmacological treatment. While such treatment can reduce the tendency of an atrium to undergo fibrillation, once such atrial fibrillation begins, however, the pharmacological treatment to stop atrial fibrillation is not practical as it is difficult for a patient to administer a pharmacological agent to stop ongoing atrial fibrillation. The fact that the pharmacological treatment is not automatic and instantaneous makes such treatment of an ongoing atrial fibrillation difficult, if not impossible.

Another method of treating atrial fibrillation is to ablate (burn) portions or patterns in the heart to stop the circus motion that is associated with atrial fibrillation. For example, circumferential patterns may be burned around the four left pulmonary veins. Disadvantageously, this method is very surgically invasive and often provides only marginal efficacy.

Still another approach is a device-based approach using a stimulator that delivers pulses through a single electrode attached to an atrium. One such method involves overpacing the atrial contraction rate to disrupt the normal atrial rhythms with the intent to shorten the long, diastolic periods and to cancel the premature atrial contractions found in a fibrillating atrium. While mildly successful, use of overpacing in a single-electrode based system can cause pacemaker-mediated, congestive heart failure.

Another device-based method uses defibrillators to shock the atrium in order to stop atrial fibrillation. The high levels of energy used to produce the shocks, however, can cause pain and otherwise be disconcerting to a patient. Methods have been described which use lower, less discernable energy levels, as described in U.S. Pat. No. 5,620,468 issued to Mongeon, et. al., which patent is incorporated herein by reference in its entirety. Other patents or publications which are relevant to the treatment of atrial fibrillation (all cited in the '468 patent) include: U.S. Pat. No. 3,937,226; PCT No. U.S. 92/02829 (Publication No. WO 92/18198); U.S. Pat. No. 5,356,425; and U.S. Pat. No. 5,334,221.

It is apparent that what is needed is an improved device-based therapy that can suppress the onset of atrial fibrillation and also treat atrial fibrillation once it is detected.

SUMMARY OF THE INVENTION

The present invention addresses the above and other needs by providing a system and method for applying at least two cathodic electrodes (or electrode contacts) to the target atrium. This multi-site stimulation system and method can (a) stop atrial fibrillation when it is detected, (b) suppress the onset or atrial fibrillation by stimulating the multiplicity of electrodes after the natural onset of atrial contraction or (c) pace the atrium and also suppress the onset of atrial fibrillation through the multi-electrode stimulation method. Alternatively, the system may also be capable of performing modes (a) and (b) or modes (a) and (c).

In one aspect of the invention, there is provided an advanced anti-arrhythmia system employing multiple stimulation sites on a single atrium. The system can comprise: a detection circuitry for sensing atrial fibrillation in the heart; at least two electrodes (or a multiplicity of electrodes), which electrodes are attached to the target atrium and a stimulus generator that can deliver stimulus through each electrode in response to, for example, detected atrial fibrillation. The stimulus delivered at each electrode (or stimulation channel) is independently controlled. By "independently controlled", it is meant that at minimum, the stimulus delivered at each channel or electrode can be independently varied with respect to amplitude, pulsewidth and initiation time. These values can be programmed and stored in memory within an implantable stimulator.

As additional embodiments, the detection circuitry may also be able to detect the termination of atrial fibrillation. In general, to determine the onset and termination of atrial fibrillation, the detection circuitry must also be able to monitor the cardiac cycle. Additional electronic circuitry may be included to deactivate or turn off delivery of stimulation through all of the electrodes. The stimulus generator can be configured to deliver stimulation through at least two electrodes simultaneously. Alternatively, the stimulus generator can be configured to deliver stimulus through each electrode in a sequential, timed steps. One of the at least two electrodes (or multiplicity of electrodes) can be used as both a sense and stimulation electrode, in a time-multiplexed manner. The function of sensing and stimulation cannot be implemented exactly at the same time. The stimulus delivered at the at least two electrodes can occur in synchrony with respect to the cardiac cycle, or they may occur asynchronously with the cardiac cycle. The stimulus delivered at one or more electrodes may not necessarily be a stimulus pulse but may be a train of stimulus pulses, i.e., a "stimulus burst." The stimulus used is preferably "biphasic," meaning it has a negative and positive phase components, although the invention could be practiced with a uniphasic stimulus as well.

In a further embodiment, an anti-arrhythmia system for suppressing the onset of atrial fibrillation is provided, the system comprising: electronic circuitry for detecting the cardiac cycle of a target atrium; at least two electrodes, which electrodes are attached to the target atrium; and a stimulus generator having at least two independently controllable stimulation channel outputs. The electronic circuitry for detecting the cardiac cycle can be responsive to atrial contraction and in communication with the stimulus generator that can deliver timed stimulation through each of the at least two electrodes to suppress the onset of atrial fibrillation. In one embodiment of the system, the system may be used to not only pace the atrium but, at the same time, suppress any onset of atrial fibrillation.

In another aspect of the invention, there is provided a method (Mode I) of stimulation for detecting the onset of atrial fibrillation and stopping the atrial fibrillation. The method comprises: attaching at least two electrodes on one atrium; detecting atrial fibrillation; delivering a constant-current, but independently settable stimulus through each of the at least two electrodes; detecting the cessation of atrial fibrillation; and deactivating the delivery of stimulus to each electrode in response to the cessation of atrial fibrillation.

In a further embodiment of the method (Mode II) of the present invention, there is provided a method of suppressing the initiation of atrial fibrillation, the method comprising: attaching at least two electrodes on a target atrium; detecting the onset of atrial contraction at the target atrium using a sense electrode; delivering a constant-current, but independently settable stimulus through each of the at least two electrodes.

In yet a further embodiment of the method (Mode III) of the present invention, there is provided a method of both pacing the atrium and suppressing the initiation of atrial fibrillation. The method comprises: providing at least two electrodes attached to a target atrium for independently delivering stimulus through the at least two electrodes; sensing cardiac activity using a sense electrode to determine when the atrium should be paced; delivering a time sequence of stimulus pulses through each of the at least two electrodes to contract the atrium. A pacing pulse can be applied through the first electrode to initiate an atrial contraction and then concurrently or in sequence, a stimulus may be applied through the second electrode, then through the third electrode, etc. This will result in contracting the atrium faster than its native contraction and forestalling the onset of atrial fibrillation in the atrium.

In other embodiments, the system of the present invention can be switched to operate in Mode I, Mode II or Mode III, or combinations of Modes I and III or Modes I and II.

It is a feature of the present invention to provide a system and method for implementing a multi-site, multi-mode, atrial, anti-arrhythmia stimulation therapy that can more precisely control the application of stimulus in terms of (a) spatially, as stimulation is applied to more than one site in or on the atrium; (b) temporally, since the stimulus may be applied simultaneously or in timed sequence among a multiplicity of stimulation channels (or electrode contacts); and (c) precise energy level applied, because the parameters of the stimulus may be varied with respect to pulsewidth and amplitude using a current-controlled stimulus. In addition, additional flexibility can be provided in that the system may provide a single stimulus pulsewidth or a stimulus pulse burst.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1A:
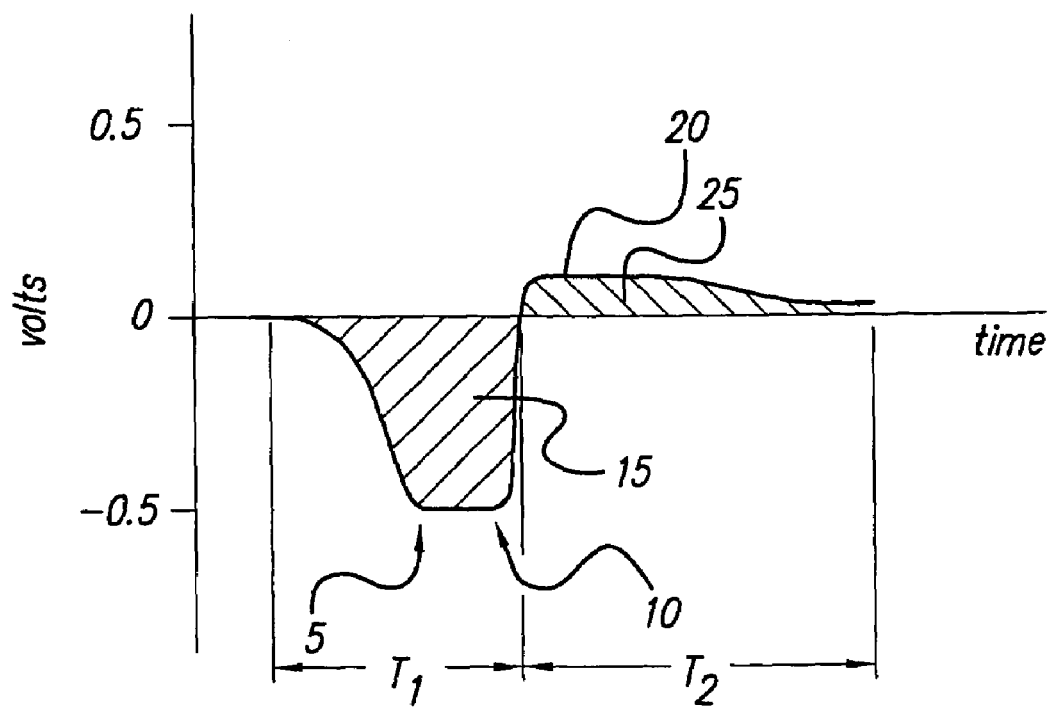
FIG. 1A shows a graphed representation of constant-voltage stimulus pulse commonly used in cardiac pacing.

The following description is of the best mode presently contemplated for carrying out the invention. This description is not to be taken in a limiting sense, but is made merely for the purpose of describing the general principles of the invention. The scope of the invention should be determined with reference to the claims.

Use of a constant-voltage, i.e., voltage-controlled, stimulation is prevalent in the field of cardiac pacing. Constant-voltage stimulation is adequate for pacing heart tissue because the function of such pacing is essentially to "jump start" cardiac contraction. The function of stimulation to treat atrial fibrillation, however, differs in significant respects. Unlike conventional cardiac pacing, suppressing the onset of atrial fibrillation or stopping ongoing atrial fibrillation does not require depolarizing cardiac tissue at a single point to "jump start" cardiac contraction. Instead, stimulation is applied to a large surface of atrial tissue that is in various stages of depolarization and repolarization. Treating atrial fibrillation, in accordance with the present invention, can require that more than one atrial area be stimulated to best prevent circus conduction which characterizes atrial fibrillation. In addition, the electrodes used to treat atrial fibrillation can have greater surface area than a conventional pacing electrode.

Another important difference between cardiac pacing is that only a single electrode needs to be attached to the heart in order to implement atrial pacing. In some cases, an electrode may be placed on an atrium and one on the ventricle for dual-chambered pacing.

In contrast, to treat atrial fibrillation, in accordance with the present invention, two electrodes or electrode contacts attached to a single target atrium. A multi-site stimulation system is desirable because: (1) it better controls the spatial circus conduction motions that characterize atrial fibrillation and (2) it better deals with intervening structures or abnormalities which can interfere with proper atrial stimulation. For example, the Pectinate muscle fibers, the Crista Terminalis and the Eustachian valve are right atrial anatomical structures which can interfere with the proper stimulation of the right atrium. In such a case, use of a single electrode to control atrial fibrillation will not be as effective as using two or more electrodes attached to a single atrium.

The present invention accommodates intervening structures and anatomical irregularities of the left and right atria by using at least two independently programmable stimulation channels that can deliver different stimuli to two electrodes at different sites on the target atrium. The use of at least two electrodes which can be independently controlled or programmed allows: (a) spatial specificity; (b) time specificity; and (c) stimulus energy level specificity. There is spatial specificity because two or more electrodes can cover a greater space over the atrium and accommodate anatomical irregularities in the atrium better than a single electrode. There is time specificity with at least two independently settable stimulus through multiple (at least two) electrodes because each electrode can deliver a stimulus that begins at a different time and ends at a different time. The energy level of each stimulus may be precisely and variously programmed for different pulsewidth and amplitude. The stimulus through an electrode may be optionally composed of a train of pulses as opposed to a single stimulus pulse. In addition, the present invention can also employ current-controlled stimulus as opposed to voltage-controlled stimulus, for more precise delivery of stimulus energy levels through an individual electrode (electrode contact).

FIG. 1A shows a representation of a constant-voltage, biphasic stimulus pulse 5 which is conventionally used in cardiac pacing and can be used in other tissue stimulation therapies. For general cardiac pacing, only a single such stimulus pulse is required to adequately pace an atrium or ventricle in the heart to treat various arrhythmic heart ailments.

The first phase 10 of the stimulus pulse 5 is a constant voltage (negative polarity) portion having a duration $T_1$ and an area 15. The second phase 20 switches to positive polarity and has an area 25. The second phase 20 can have a longer duration $T_2$ than $T_1$, the duration of the first phase 10. The area 15 and area 25 should be approximately equal in order to have charge balancing. The second phase 20 is not a necessary part of the stimulus but is often applied to provide a biphasic pulse. "Biphasic pulse," as used herein, means a stimulus pulse which traverses both negative and positive polarities as a function of time. It is believed that applying such a charge-balanced, biphasic stimulus can effectively prevent electrode corrosion and prevent the build-up of harmful charges in the tissue.

It is important to understand that because most stimulation is biphasic, an electrode attached to the heart is both a cathode and an anode at different times. However, generally speaking, stimulation is elicited by the first, cathodic phase 10 of the biphasic stimulus 5, and therefore because tissue stimulation is elicited by the cathodic phase, an electrode delivering a stimulus with a first, cathodic phase 10 (as opposed to a first, anodic phase) is referred to as a "cathode." When two electrodes are attached to an atrium and the first electrode has first cathodic phase 10 while the second electrode (or electrode contact) has an opposite anodic polarity during the first phase, the first electrode is deemed the "cathode" and the second electrode (or electrode contact) is deemed the "anode." When the housing of an IPG is used as a return, indifferent electrode, in combination with an electrode (or electrode contact) placed on the atrium, then the housing is the anode and the electrode is the cathode. This definition of a "cathode electrode" and "anode electrode" will be used herein.

Figure 1B:
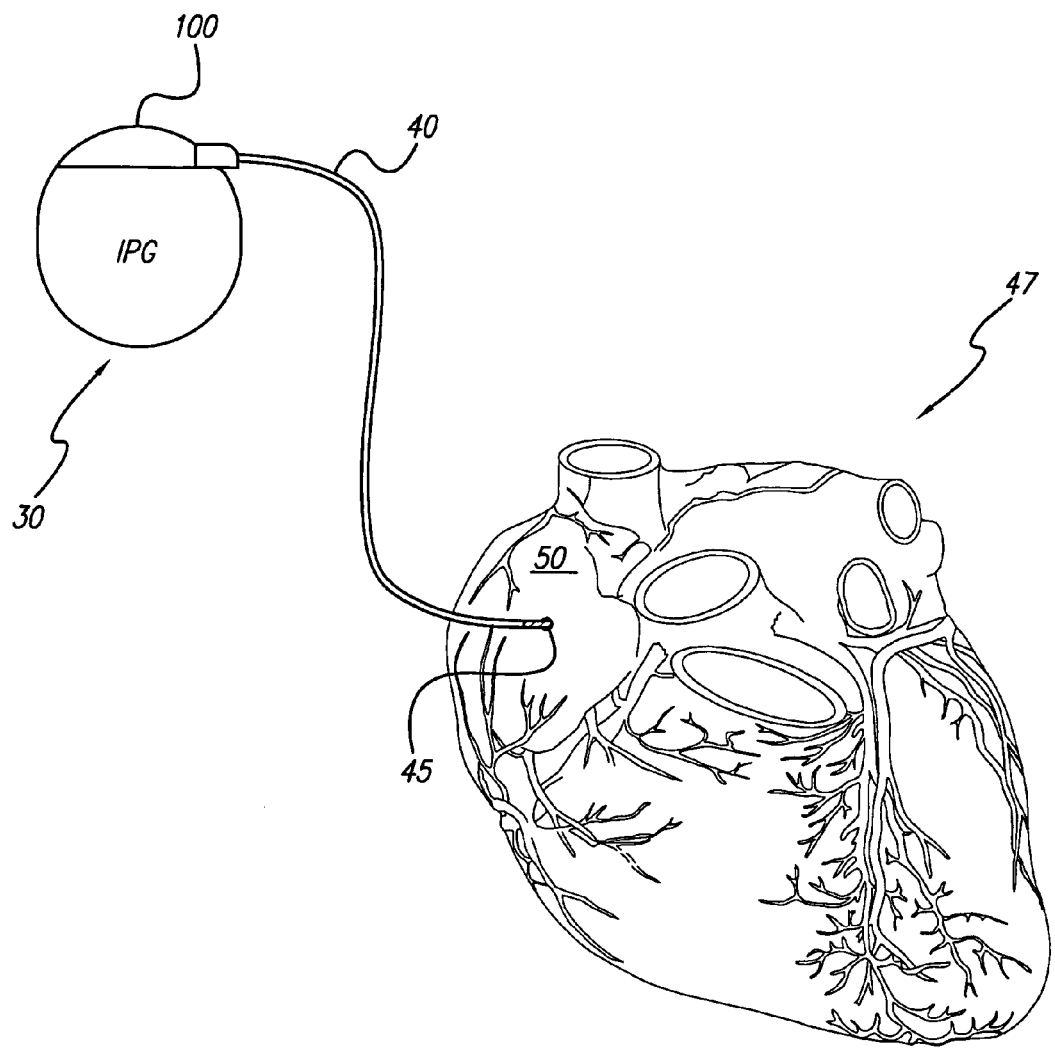
FIG. 1B shows a conventional cardiac pacing system with a single lead and electrode connected to an atrium.

FIG. 1B shows one example of a conventional, cardiac pacing system consisting of an implantable pulse generator (IPG) 30, a single cardiac pacing lead 40 having an electrode 45 at the lead distal tip, which electrode 45 contacts the wall of an atrium 50. In other cases, a single lead/electrode is coupled to a single ventricle. In dual-chamber pacing, however, two leads may be used, one lead to pace an atrium and other lead to pace a ventricle. Generally, in conventional cardiac pacing, two stimulation (cathode) electrodes are never placed onto the same atrium or the same ventricle.

When constant-voltage stimulation is used, the voltage potential applied at the tissue-electrode interface remains constant. Ohm's Law states: V=IR, where V is the voltage, I is the current and R is the resistance (or impedance). In accordance with Ohm's Law, if the voltage remains constant (as in a constant-voltage stimulus) while the resistance (or impedance) changes, then the current must change. For example, if lead impedance is reduced by increasing the electrode surface area while the voltage is set at a constant value, disadvantageously, the current applied to the tissue increases.

Figure 2A:
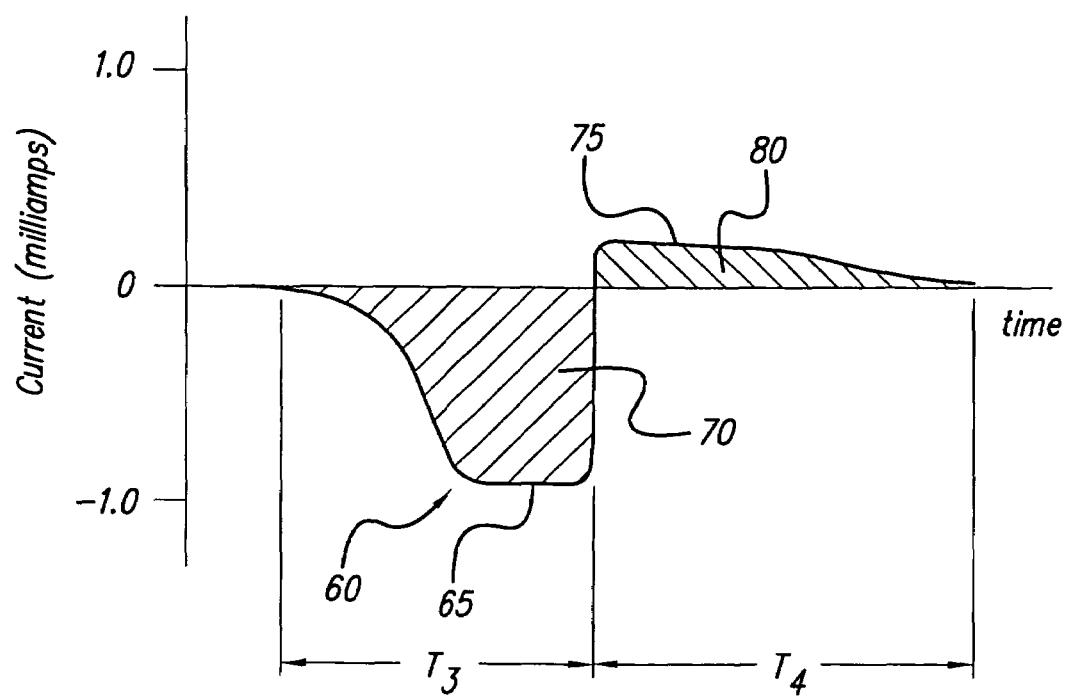
FIG. 2A shows, in accordance with the present invention, a graphed representation of a biphasic, constant-current stimulus that may be used to treat atrial fibrillation.

FIG. 2A shows a representation of a constant-current (current-controlled) stimulus pulse 60 that may be employed with the present invention. The first phase 65 of the pulse 60 has negative polarity. The second phase 75 is positive and charge balances the first phase 65. The areas 70 and 80 within the outline of the pulse should be about equal to achieve charge balancing. Unlike a constant-voltage pulse which is conventionally used in cardiac pacing, a constant-current pulse advantageously injects the same quantity (or rate) of charge into tissue regardless of tissue impedance or impedance of the electrode. Thus, the quantity of charge dissipated into a tissue can stay the same regardless of the electrode surface area or the presence of tissue irregularities between the electrode and the target cardiac tissue. In short, the charge delivery to a portion of target cardiac tissue may be more easily controlled, even if the lead or tissue impedance varies.

Another important difference between cardiac pacing and stimulation to treat atrial fibrillation, as in the present invention, is that in the latter case, a train of pulses may be delivered to provide a "burst" of stimulus pulses. Such a stimulus burst can be more effective in stopping atrial fibrillation than applying a single pulse, because the burst of pulses can be more effective in preventing a portion of an atrium from repolarizing. By stopping atrial repolarization for a brief period, circus conduction motion characterizing atrial fibrillation can be stopped. It should be emphasized that in conventional cardiac pacing, pulse bursts are never used to pace the heart, as it is not a goal to prevent atrial repolarization.

Figure 2B:
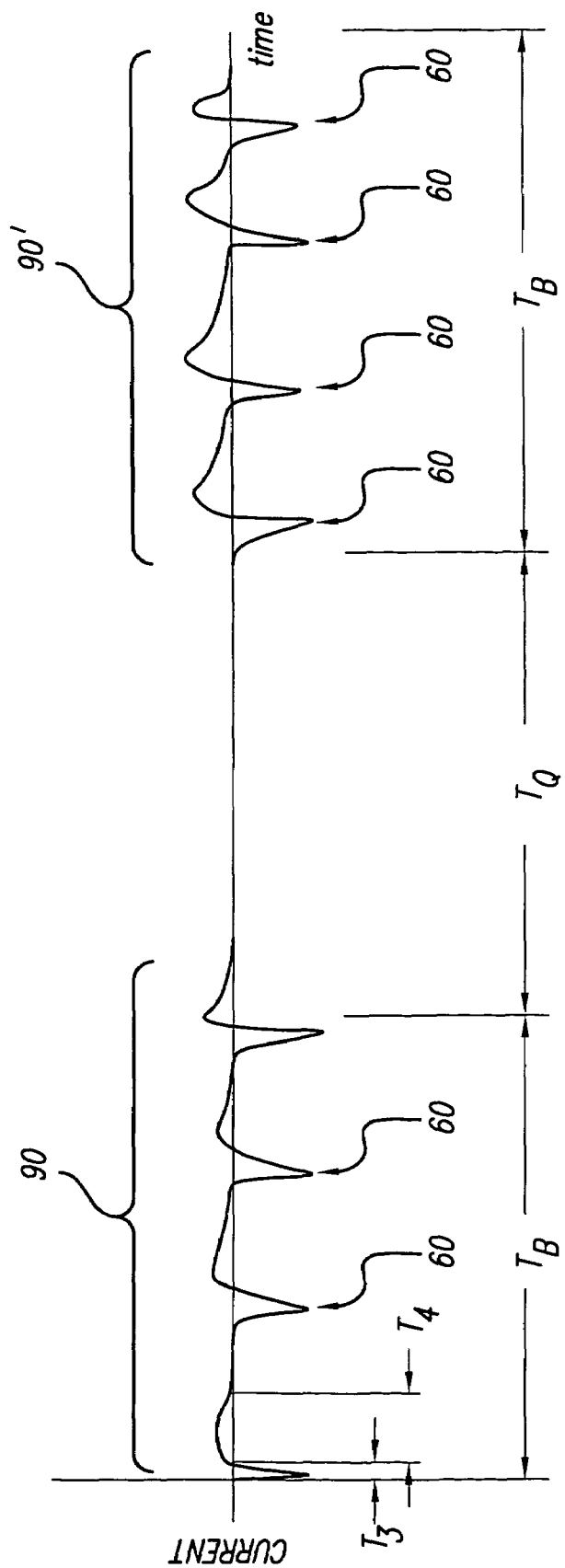
FIG. 2B shows, in accordance with the present invention, a train of biphasic pulses or "burst" of pulses, which pulses are depicted in FIG. 2A.

FIG. 2B shows such a stimulus burst composed of a multiplicity of stimuli depicted in FIG. 2A. Two trains or bursts 90 of stimulus pulses 60 are shown. Each burst 90 lasts for a total duration of $T_B$. The quiescent period between bursts is shown as a time duration $T_Q$. A single burst 90 may be sufficient to terminate atrial fibrillation. More than one such pulse burst, from the same electrode or from different electrodes, however, can be used to treat atrial fibrillation.

FIGS. 3A-D shows exemplary representations of electrode configurations that may be used as part of the anti-arrhythmia system of the present invention.

Figure 3A:
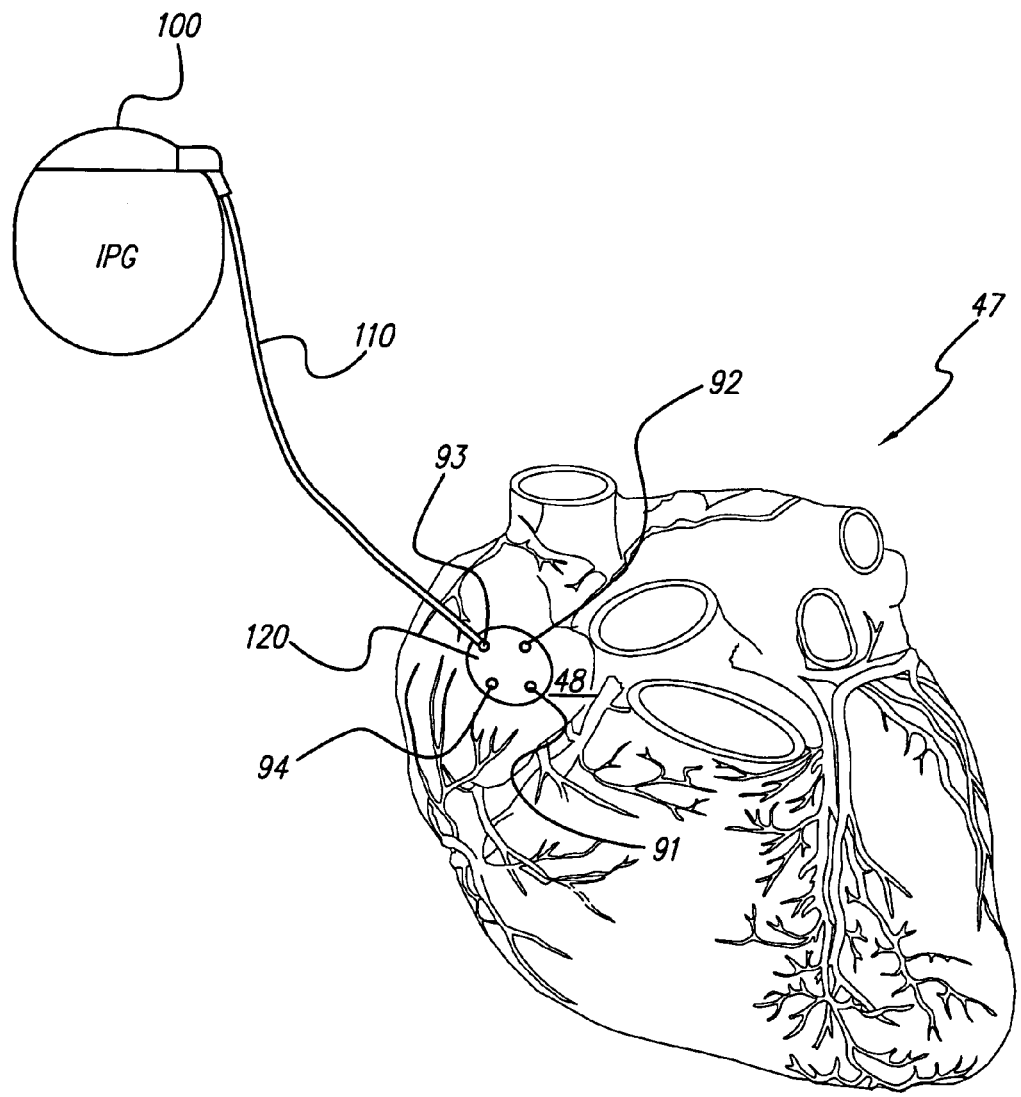
FIG. 3A shows, in accordance with the present invention, one embodiment of an exemplary lead system with a four electrode array placed over a target atrium.

FIG. 3A shows, in accordance with the present invention, one embodiment of an anti-arrhythmia system comprising an implantable pulse generator 100 which is capable of delivering a single stimulus pulse or a burst of pulses in programmed intervals. The example shown provides an example lead 110 connected to the output of the IPG 100. The lead 110 has four electrodes 91, 92, 93 and 94 placed onto a substrate 120 to create an electrode array. Each of these four electrodes can be programmed to function as a cathode (negative polarity), anode (positive polarity) or be turned off (high impedance mode). The IPG housing may also function as an indifferent (positive polarity) return electrode.

The electrodes are characterized as cathodes because stimulation of cardiac tissue occurs as a result of applying the cathodic phase 65 first through the electrode which causes stimulation. An electrode configuration in which the IPG 100 housing is used as a return or indifferent electrode is loosely defined as a monopolar configuration. Electrode stimulation wherein the IPG 100 housing is not used as an electrode is loosely defined as a bipolar configuration.

Bipolar stimulation may be performed with the system shown in FIG. 3A. Some examples of electrode polarities during time duration $T_3$ (as shown in FIG. 2A) are provided in Table 1:

TABLE 1

Sample bipolar stimulation during treatment of atrial fibrillation during time duration $T_3$.

| | Example 1 | Example 2 | Example 3 | Example 4 |
|---|---|---|---|---|
| electrode (91) | (−) channel 1 | (−) channel 1 | (+) | (−) channel 1 |
| electrode (92) | (+) | (−) channel 2 | (−) channel 1 | (+) |
| electrode (93) | (−) channel 2 | (+) | (−) channel 2 | (−) channel 2 |
| electrode (94) | | | (−) channel 3 | (−) channel 3 |

To enable bipolar stimulation, generally at least one electrode must be a cathode (negative polarity) and one must be an anode (positive polarity) during time duration $T_3$. The examples shown in Table 1 show some possible configurations of electrode polarities, wherein at least two electrodes in each example function as cathodes (negative polarity). This meets the requirement that the anti-arrhythmia system of the present invention possess two independently controllable stimulation channels. Two distinct locations of the atrium are thereby treated with independently applied stimulation. Such treatment at multiple sites can more effectively terminate circus motion in the atrium as compared with stimulating only a single atrial site.

Table 2 provides examples of monopolar electrode configurations, in accordance with the present invention, using the same four electrode system shown in FIG. 3A. In each of these examples, at least two electrodes are cathodes during time duration $T_3$. The IPG housing acts as the indifferent (sink or return) anodic electrode.

TABLE 2

Sample monopolar stimulation during treatment of atrial fibrillation during time duration $T_3$.

| | Example 5 | Example 6 | Example 7 | Example 8 |
|---|---|---|---|---|
| electrode (91) | (−) channel 1 | (−) channel 1 | | (−) channel 1 |
| electrode (92) | | (−) channel 2 | (−) channel 1 | (−) channel 2 |
| electrode (93) | (−) channel 2 | | (−) channel 2 | (−) channel 3 |
| electrode (94) | | | (−) channel 3 | (−) channel 4 |

Figure 3B:
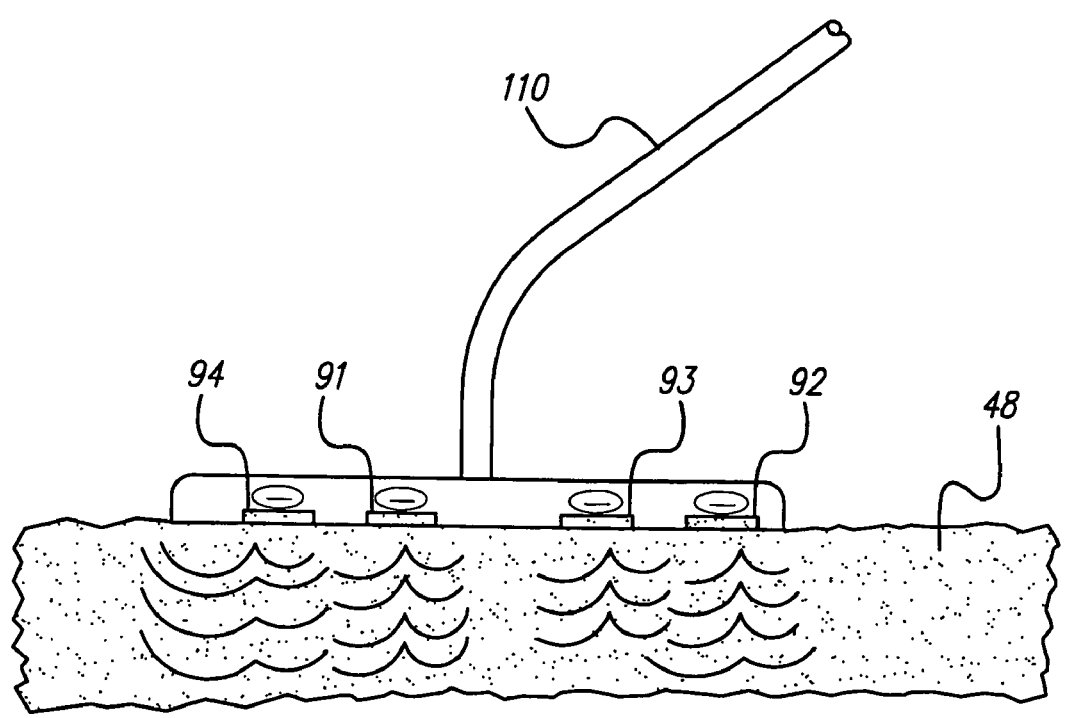
FIG. 3B shows a cross-sectional view of the atrium and lead of FIG. 3A showing the current flow pattern within the atrium wall.

FIG. 3B shows a depiction of the lead 110 and a cross-sectional view of an electrode array with electrodes 91, 92, 93 and 94. This view depicts Example 8 of Table 2, wherein all four electrodes operate as cathodes during $T_3$ shown in FIG. 2A. Referring again to FIG. 3B, the current field lines penetrate the cardiac wall 48 and return to the IPG housing (not shown) which acts as the indifferent electrode.

The system of the present invention therefore is characterized by at least two independently controllable, cathodic electrodes placed on different portions of the atrium 48 to stop conduction circus motion. To independently stimulate the two electrodes, the IPG must contain at least two independently controlled, programmable channels. Specifically, the two channels may be separately programmable for pulsewidth, pulse amplitude, pulse burst duration, $T_B$, the quiescent time, $T_Q$, pulses per second, as well as onset of each pulse or pulse train in a channel relative to activity in another channel. The available choice of stimulation configuration may be monopolar (wherein the IPG housing is an indifferent electrode) or bipolar (wherein the IPG housing is not an electrode). The electrode stimulus may be current controlled and can be obtained by using current sources contained in the IPG, which current sources can deliver a constant-current pulse as shown in FIG. 2A.

It is noted that examples in Table 1 and 2 provide two or three independent, current-controlled, stimulation channels. However, a system employing three or more independent programmable channels can be used in accordance with the present invention and such multi-channel, atrial, anti-arrhythmia stimulation systems are intended to be included as part of the present invention.

Furthermore, applicable lead configurations are not limited to the lead configuration shown in FIG. 3A. Other embodiments of the lead, in accordance with the system of the present invention, can include a substantially flat, conformable, coiled-type lead that can be placed over the surface of an atrium. At least two electrodes can be attached to the underside of the flat coil and the two electrodes can be electrically coupled to at least two stimulation channels in the IPG. Such a lead assembly permits use of a single lead, with multiple electrode contacts, and having multiple conductor wires connected to the IPG, while permitting the contact portion of the lead assembly to conform to the surface of the heart.

Figure 3C:
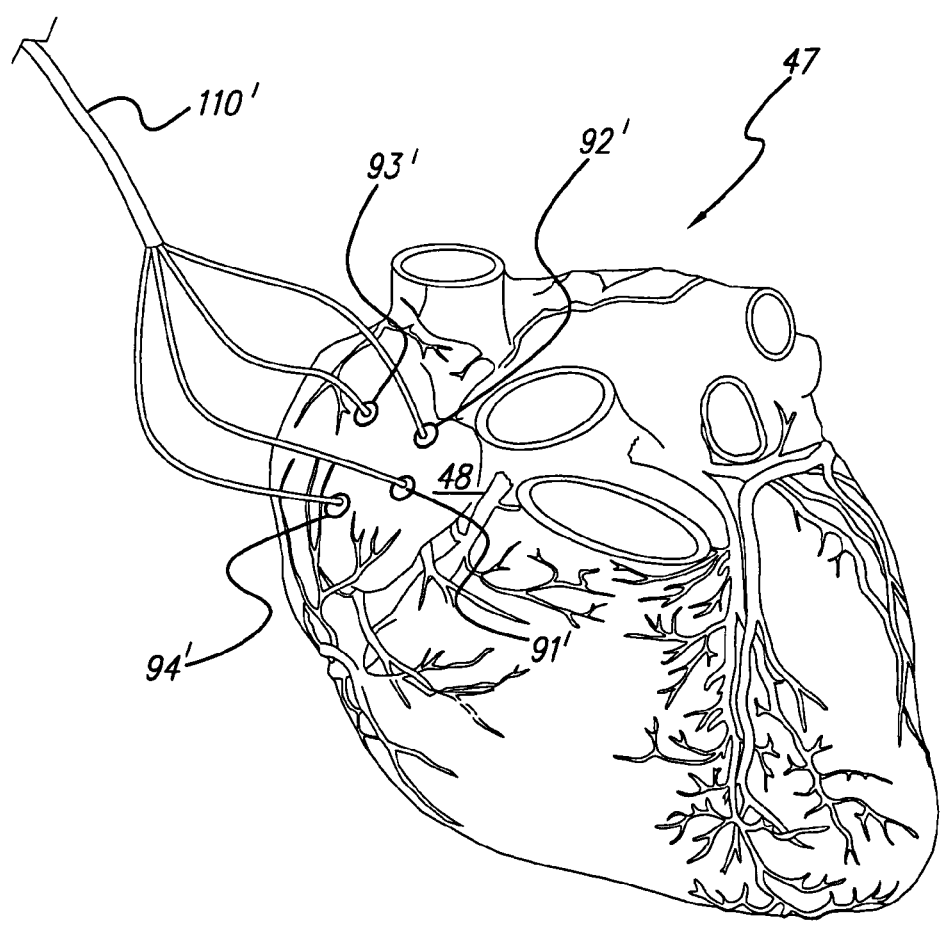
FIG. 3C shows, in accordance with the present invention, another embodiment of an exemplary lead system in which a single lead branches into four separate leads, each lead having one electrode.

FIG. 3C shows another embodiment of a lead that may be used in the present system. The lead 110' branches into four, separate, atrial branch leads, wherein at least one electrode 91', 92', 93' and 94' is distally attached to each of the branch leads. Alternatively, in another embodiment, four separate leads may be employed, each lead having a single electrode at the distal end and attached to the target atrium. In yet another embodiment, two leads, each having two electrodes attached to the distal end of each lead, can be used. These examples all provide a total of four electrodes attached to the atrium. It can be seen that similar lead/electrode configuration strategies can be adapted to systems having two, three, five or more electrodes by mixing and matching the types of leads used.

Figure 3D:
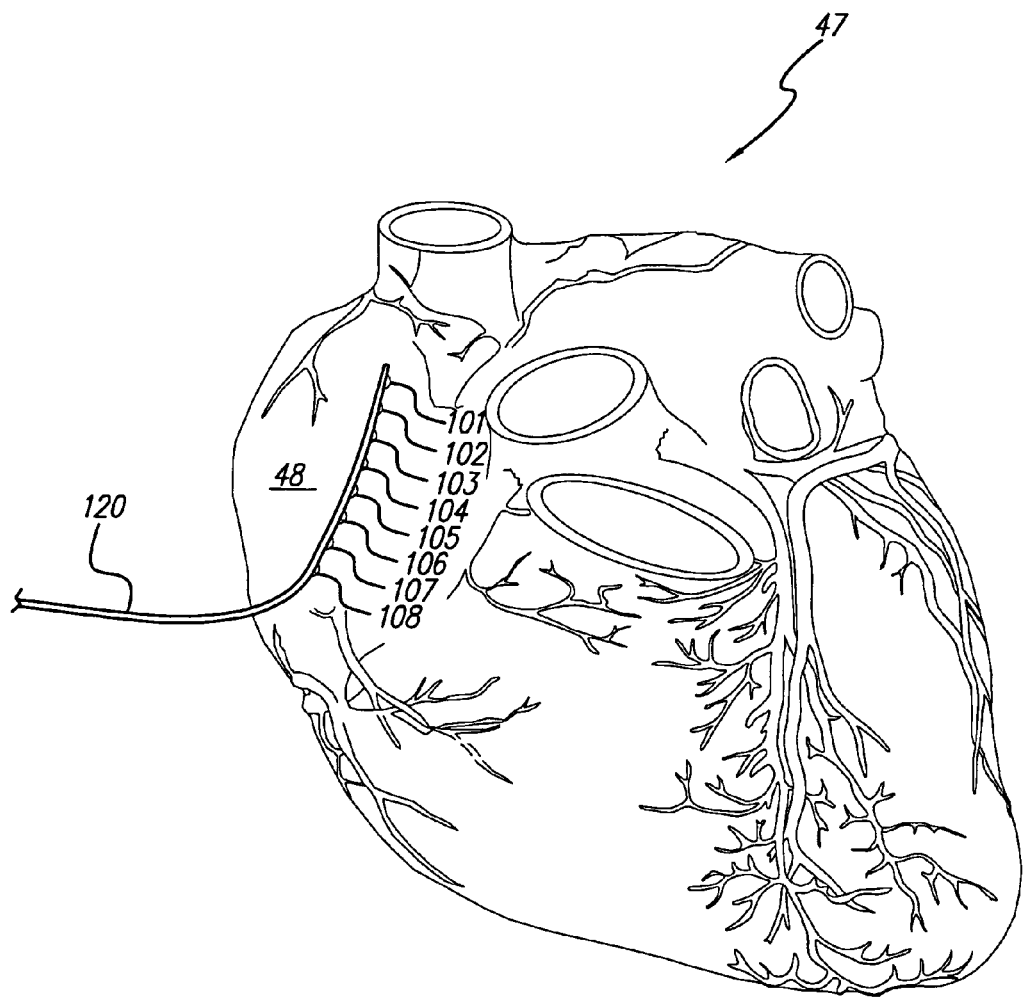
FIG. 3D shows, in accordance with the present invention, another embodiment of an exemplary single lead which is linear and has in-line electrodes along the lead carrier.

FIG. 3D shows an exemplary, single lead which has an in-line eight electrode array, with electrodes 101 through 108. The electrodes can be placed on the distal portion of the lead 120 and may be positioned with a constant inter-electrode spacing. The electrode array can be attached over the surface of the outer wall of a target atrium in a substantially vertical position relative to the heart. Alternatively, the lead may be attached to the inside wall of the atrium, again in a substantially vertical position relative to the heart.

Figure 4:
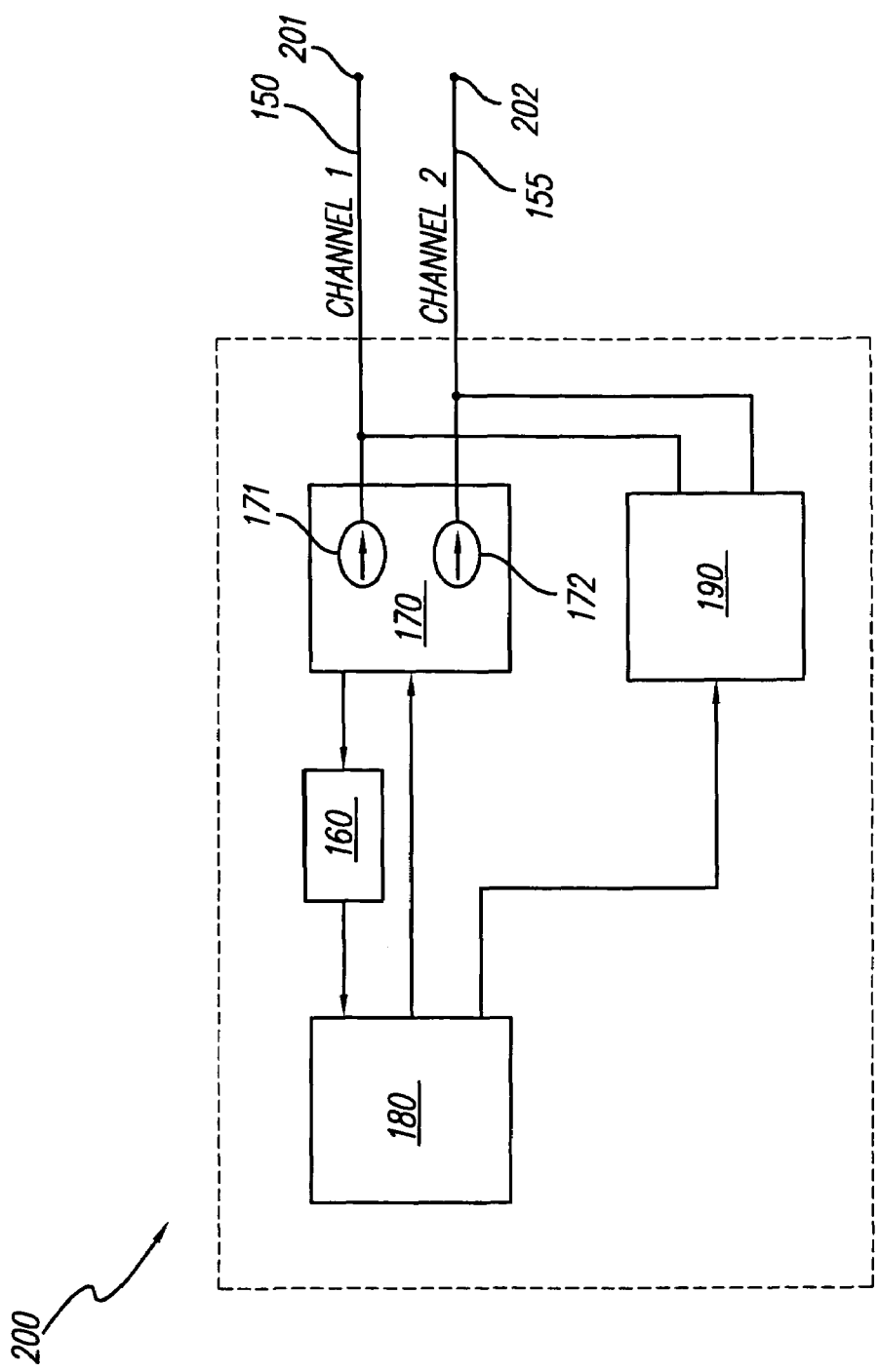
FIG. 4 shows, in accordance with the present invention, a block diagram representing an anti-arrhythmia system for sensing atrial fibrillation and delivering current-controlled stimulus to the fibrillating atrium.

FIG. 4 shows a simplified block diagram 200 of an atrial anti-arrhythmia stimulation system, in accordance with the present invention, which system has a detection circuitry 160 that can sense and analyze the atrial and cardiac electrical activity and detect atrial fibrillation. The system can comprise a single lead, with at least two cathodic electrodes, as in FIG. 3A or FIG. 3B, or a multiplicity of N leads of a kind depicted in FIG. 3C, which electrodes or leads can be connected to a multi-channel stimulator that preferably delivers a constant-current stimulus through each of the multiplicity of electrodes that can define a separate channel. In the example shown, two leads are depicted, 150 and 151, each lead defining a single channel. Lead 150 has a distal electrode 201 and lead 155 has distal electrode 202. Each channel is independently programmable with respect to stimulation parameters, e.g., pulsewidth, pulse repetition rate (pulses per second), and amplitude, to provide constant current from 0 to 5.0 milliamperes.

A constant-current stimulus can be provided by an amplifier 170 that is coupled to constant-current sources 171 and 172. In addition, a detection circuitry 160 may be included for detecting atrial fibrillation in the target atrium, which detection circuitry can use leads 150 and/or 151 as sense leads in addition to stimulation leads or another dedicated sense lead (not shown) may be used. Control logic 180 accepts input from detection circuitry 160 to signal when atrial fibrillation is detected. The control logic 180 then sends a signal to the amplifier 170 to turn on and set the channel and electrode configurations, whereby each electrode is set as a cathode, anode, or off, based on the pre-programming of stimulation parameters. A control signal can be sent to the burst control circuitry 190 which can open and close the switches connecting the current source 171, 172 to the electrodes 201 and 202 at programmed stimulus frequencies (pulses per second) to provide an appropriately timed burst of stimulus pulses.

In alternative embodiments, a separate lead having an electrode attached to the atrium may be used to sense atrial fibrillation activity. In other embodiments, an electrode placed on either the left or right ventricle may be used to detect ventricular depolarization and repolarization, when atrial stimulation is to be conducted synchronously to the cardiac cycle.

In a first mode (Mode I) of a method operation, each of at least two, independent stimulation channels (using at least two electrodes) may be used to asynchronously or synchronously stimulate an atrium upon the detection of an atrial fibrillation event. When atrial fibrillation is detected with a sense electrode, at least the second electrode delivers a pulse or burst stimulation which can help contract another part of the atrium, or keep the atrium in a hyperpolarized state to stop an ongoing atrial fibrillation. The detection circuit 160 can be continuously in operation sensing the atrium and detecting atrial fibrillation activity. Here, "asynchronously" refers to stimulation that is not specifically timed to the sequence or phases of the cardiac cycle but, instead, is applied any time after atrial fibrillation is detected in an atrium. In addition, because each channel is independently programmable, one stimulation channel may be simultaneously stimulating (on) with respect to another stimulation channel. Alternatively, one stimulation channel may initiate a stimulus pulse or burst of pulses at a different time from another stimulation channel to yield a sequential, timed stimulation through, for instance, different electrodes attached to the atrium.

In a second mode (Mode II) of operation, the system may preemptively suppress the onset of atrial fibrillation in patients who have a predisposition to atrial fibrillation. The detection circuit 160 connected to at least one electrode, which is operating as a sense electrode, can be set to analyze the atrial contraction cycle. When atrial contraction is first detected in the sense electrode, a subsequent, timed sequence of stimuli may be delivered to at least the second electrode or other available electrodes (including the first electrode, which may operate as a stimulating electrode). The stimulus delivered to the second electrode or other electrodes can help contract (pace) a portion of the atrium. If the stimulus is being used to pace the heart, generally a single pulse is preferred. Such pacing can prevent circus conduction in the atrium. Otherwise, the stimulus delivered to the second electrode or other electrodes may be a burst or train of pulses which does not contract the heart but simply suppresses circus conduction in the atrium.

In still a third mode (Mode III) of operation, the system may pace (initiate contraction of) an atrium using stimulation from at least two electrodes placed on the outer surface or inner wall of the atrium using a single lead with a multi-electrode array as shown in FIG. 3D. Operating, for example, in a monopolar configuration where the IPG housing functions as an indifferent electrode, a precise timed, sequence of stimulation through each electrode is used to control the rate of contraction throughout the target atrium. The sequential pacing through the electrodes can be timed to preempt the native (usually too slow) speed of an atrial contraction while at the same time suppressing the onset of atrial fibrillation. Atrial fibrillation is suppressed because the effect of the sequential pacing is to force more rapid contraction of the entire atrium and shorten the atrial contraction cycle, thereby reducing the chance for circus motions.

As further explanation, referring to the lead in FIG. 3D, after the ventricles have completed contraction, as detected by a sense electrode on the heart, a first pulse stimulus, $S_1$, can be applied through electrode 101. After a time interval, $I_2$, as measured from the beginning of the first stimulus, $S_1$, a second pulse stimulus, $S_2$, can be applied through electrode 102. After another time interval, $I_2$, as measured from the beginning of the second stimulus, a third pulse stimulus, $S_3$, can be applied through electrode 103, and so on, until the second-to-last stimulus, $S_{N-1}$ is applied. After an interval, $I_{N-1}$, as measured from the beginning of the second-to-the-last stimulus, a last pulse stimulus, $S_N$, is applied to the last electrode 108. N represents the number of electrodes on the type of lead shown in FIG. 3D. N-1 is the number of time intervals $I_1$, through $I_{N-1}$, which may be programmed to the same time values or to different time values, depending on the inter-electrode spacing on the lead carrier.

It may be seen that S1, S2 ... SN may each be a single pulse or each a train of pulses. It may also be possible to have a mix of single pulses and trains of pulses. It may be possible that the adjacently timed stimulus, e.g. S1 and S2, S4 and S5, S6 and S7, etc., may actually overlap wholly or partially during a time interval.

Specifically, as shown in FIG. 3D, N=8, with equally spaced electrodes, there are N-1 time intervals that can be programmed. One method of selecting the values for the time intervals, $I_1$, through $I_{N-1}$, is to take the total target time for right atrial depolarization, $T_{target}$, and divide this value by the number of electrodes, N, to get an approximate time interval that can be applied to each time interval from $I_1$ through $I_{N-1}$, $T_{target}$ has to be pre-programmed to a predetermined value in an IPG. For example, $T_{target}$ may represent the total time elapsed during a right atrial depolarization, when an individual is resting. Generally, in an average, resting cardiac cycle, the right atrial depolarization occurs over about 40 milliseconds. Thus, for a lead depicted in FIG. 3D, having eight electrodes equally spaced apart, each time interval, $I_1$, through $I_{N-1}$, can be about 5.5 milliseconds long. Of course, the values of $T_{target}$ will vary, depending on the activity of the individual. If a rate responsive circuit is incorporated into the IPG, the rate responsive circuit can continuously adjust the value of $T_{target}$ as a function of the individual's activity or movement averaged over some predetermined time and/or the sensed duration of the cardiac cycle.

In general, artificially contracting (pacing) the atrium in this manner requires that the timed sequence of stimulation through the multiplicity of electrodes causes the atrium to contract faster than if the atrium were to naturally contract without artificial pacing. This method of directed cardiac pacing may be suitable to treat a dilated atrium that has a long conduction length and is thus susceptible to atrial fibrillation.

It is emphasized that the above example is only one implementation of the present invention. Different types of leads may be used having variable inter-electrode spacing. The lead can be positioned in different orientations on the atrium other than as shown in FIG. 3A or FIG. 3D, depending on the pathology of the heart. Not all electrodes need to be activated in a single, atrial contraction cycle; some of the electrodes may not be used. For example, there may be a patch of cardiac tissue over which an electrode is placed that cannot be stimulated. In some pathologies of the heart, it may be preferable to stimulate some of the electrodes simultaneously, instead of in sequential, timed steps. It is, therefore, important that the IPG is capable of stimulating each electrode through independently controllable stimulation channels, since the precise, optimal sequence of stimulation through the multiplicity of (at least two) electrodes will vary greatly depending on patient pathology.

In summary, a stimulation system is provided which comprises at least two electrodes attached to a single target atrium. Independent, current-controlled stimulation can be applied through these at least two electrodes, synchronously or asynchronously in relation to the depolarization-repolarization phase of the ventricles or the target atrium. The stimulation may be applied simultaneously through at least two electrodes (or a multiplicity of electrodes) or, alternatively, in sequential, timed steps.

Three methods (modes) of anti-arrhythmia stimulation therapy are provided in the present invention. Mode I detects and stops atrial fibrillation. Mode II preemptively suppresses the onset of atrial fibrillation but does not pace. Mode III actively contracts (paces) an atrium in a timed sequence, which shortens the time to complete an atrial contraction and thereby reduces the opportunity for conduction circus motions. Depending on the exact timing and the specific operating mode, the delivered stimulus may actually cause contraction of the atrium (pacing), or it may not contract the atrium but simply prevent the onset of circus motions.

It can be seen that the generalized system described in FIG. 4 may be used to implement only a single method for treating atrial fibrillation or a combination of two methods. For instance, Modes I and II may be operational at the same time or Modes I and III may operate at the same time. Or, it is possible to program manually or automatically switch among the single, anti-arrhythmia modes. The system described in FIG. 4 should permit all three modes to be practiced singly or in the dual modes described.

While the invention herein disclosed has been described by means of specific embodiments and applications thereof, numerous modifications and variations could be made thereto by those skilled in the art without departing from the scope of the invention set forth in the claims.

What is claimed is:

1. An anti-arrhythmia system, comprising:
    a detection circuitry for sensing atrial fibrillation in a heart;
    a stimulus generator for delivering, in response to sensed atrial fibrillation, independently controlled stimulus through each of at least two electrodes for attaching to a target atrium; and
    electronic circuitry for deactivating delivery of stimulus through all of the electrodes in response to the detection circuitry detecting the termination of atrial fibrillation and then placing the anti-arrhythmia system in an atrial fibrillation suppression mode that then delivers multiple pulses to the target atrium during the same atrial contraction, wherein the suppression mode delivers the multiple pulses timed to suppress circus conduction in the target atrium to prevent onset of atrial fibrillation without causing contraction of the target atrium.

2. The anti-arrhythmia system of claim 1, wherein the suppression mode delivers the multiple pulses concurrently to the target atrium during the same atrial contraction.

3. The anti-arrhythmia system of claim 1, wherein the suppression mode delivers the multiple pulses sequentially to the target atrium during the same atrial contraction.

4. The anti-arrhythmia system of claim 1, wherein the suppression mode delivers the multiple pulses timed to induce a faster-than-native atrial contraction to prevent onset of atrial fibrillation.

5. The anti-arrhythmia system of claim 1, wherein the stimulus generator can deliver a stimulus tat is a train of pulses through at least one electrode, the train of pulses configured to suppress onset of atrial fibrillation.

6. The anti-arrhythmia system of claim 5, wherein each stimulus in the train of pulses is biphasic.

7. An anti-arrhythmia system for suppressing the onset of atrial fibrillation, comprising:
    detection circuitry for sensing atrial fibrillation in a heart;
    a stimulus generator for delivering, in response to sensed atrial fibrillation, independently controlled stimulus through each of at least two electrodes for attaching to different locations of a target atrium; and
    electronic circuitry for placing the anti-arrhythmia system in an atrial fibrillation suppression mode that then delivers multiple pulses to the target atrium during the same atrial contraction, wherein the suppression mode delivers the multiple pulses including first and second pulses, wherein the second pulse is offset from the first pulse by a specified offset time duration that suppresses circus conduction in the target atrium to inhibit atrial fibrillation without causing a separate contraction of the target atrium.

8. The anti-arrhythmia system of claim 7, wherein the stimulus generator is configured to deliver, in an atrial fibrillation suppression mode, stimuli, $S_1, S_2 \ldots S_N$, concurrently to N number of electrodes, where N is 2 or greater, such tat occurrence of $S_1$ and $S_2$ either completely or partially overlap in a time duration, $S_2$ and $S_3$ either completely or partially overlap in a time duration, and so on, such that $S_{N-1}$ and $S_N$ either completely or partially overlap in a time duration.

9. The anti-arrhythmia system of claim 8, wherein at least one of the stimulus delivered at one electrode is a train of pulses.

10. A method comprising:
    attaching at least two electrodes on one atrium;

detecting atrial fibrillation;

delivering an independently settable stimulus through each of the at least two electrodes to stop the atrial fibrillation;

detecting the cessation of atrial fibrillation;

deactivating the delivery of stimulus to each of the at least two electrode, in response to the cessation of atrial fibrillation; and delivering, in response to the cessation of atrial fibrillation, stimulation through each of the at least two electrodes, the stimulation timed to suppress the onset of atrial fibrillation, including delivering multiple pulses timed to suppress circus conduction in the target atrium to prevent onset of atrial fibrillation without causing contraction of the target atrium.

11. The method of claim 10, wherein the delivering, in response to the cessation of atrial fibrillation, comprises delivering multiple pulses concurrently to the target atrium during the same atrial contraction.

12. The method of claim 10, wherein the delivering, in response to the cessation of atrial fibrillation, comprises delivering multiple pulses sequentially to the target atrium during the same atrial contraction.

13. The method of claim 10, wherein the delivering, in response to the cessation of atrial fibrillation, comprises delivering multiple pulses timed to induce a faster-than-native atrial contraction to prevent onset of atrial fibrillation.

14. A method of suppressing the initiation of atrial fibrillation, the method comprising:

detecting atrial fibrillation using at least two electrodes associated with different locations of one atrium;

delivering an independently settable stimulus through each of the at least two electrodes to stop the atrial fibrillation;

detecting the cessation of atrial fibrillation;

deactivating the delivery of stimulus to each of the at least two electrode, in response to the cessation of atrial fibrillation; and delivering, in response to the cessation of atrial fibrillation, stimulation through each of the at least two electrodes, the stimulation timed to inhibit atrial fibrillation, comprising delivering multiple pulses including first and second pulses delivered during the same atrial contraction, wherein the second pulse is offset in time from the first pulse by a duration that is timed to suppress circus conduction in the target atrium to inhibit atrial fibrillation without causing a separate contraction of the target atrium.

15. The method of claim 14, wherein the delivering, in response to the detecting the onset of the atrial contraction, comprises delivering multiple pulses concurrently to the target atrium during the same atrial contraction.

16. The method of claim 14, wherein the delivering, in response to the detecting the onset of the atrial contraction, comprises delivering multiple pulses sequentially to the target atrium during the same atrial contraction.

17. The method of claim 14, wherein the delivering, in response to the detecting the onset of the atrial contraction, comprises delivering multiple pulses timed to induce a faster-than-native atrial contraction to prevent onset of atrial fibrillation.

18. A method for both pacing the atrium and suppressing the initiation of atrial fibrillation, the method comprising;

providing at least two electrodes configured to be attached to different locations of a target atrium for independently delivering stimulus through the at least two electrodes sensing cardiac activity using a sense electrode to determine when the atrium should be paced; and delivering a timed sequence of stimulus pulses through each of the at least two electrodes to contract the atrium, wherein the time sequence includes first and second pulses delivered during the same atrial contraction, wherein the second pulse is offset in time from the first pulse by a duration that is timed to suppress occurrence of a circus conduction in the target atrium without causing a separate contraction of the target atrium such that the resulting atrial contraction is completed faster than the atrium's native contraction, thereby forestalling initiation of conduction circus motions.

19. The method of claim 18, wherein the delivering the timed sequence comprises delivering multiple pulses concurrently to the target atrium during the same atrial contraction.

20. The method of claim 19, wherein the delivering the timed sequence comprises delivering multiple pulses sequentially to the target atrium during the same atrial contraction.

* * * * *

UNITED STATES PATENT AND TRADEMARK OFFICE
CERTIFICATE OF CORRECTION

| | | |
|---|---|---|
| PATENT NO. | : 7,321,794 B2 | Page 1 of 1 |
| APPLICATION NO. | : 10/713511 | |
| DATED | : January 22, 2008 | |
| INVENTOR(S) | : Thacker et al. | |

It is certified that error appears in the above-identified patent and that said Letters Patent is hereby corrected as shown below:

In column 12, line 32, in Claim 5, delete "tat" and insert -- that --, therefor.

In column 12, line 58, in Claim 8, delete "tat" and insert -- that --, therefor.

Signed and Sealed this

Twentieth Day of May, 2008

JON W. DUDAS
*Director of the United States Patent and Trademark Office*